(12) United States Patent
Wenstrom, Jr. et al.

(10) Patent No.: US 9,265,519 B2
(45) Date of Patent: Feb. 23, 2016

(54) TUNNEL NOTCHER AND GUIDEWIRE DELIVERY DEVICE

(75) Inventors: Richard F. Wenstrom, Jr., Raynham, MA (US); Robert K. Breech, II, Raynham, MA (US)

(73) Assignee: DePuy Mitek, LLC, Raynham, MA (US)

( * ) Notice: Subject to any disclaimer, the term of this patent is extended or adjusted under 35 U.S.C. 154(b) by 1104 days.

(21) Appl. No.: 13/282,950

(22) Filed: Oct. 27, 2011

(65) Prior Publication Data

US 2012/0041442 A1 Feb. 16, 2012

Related U.S. Application Data

(62) Division of application No. 10/708,467, filed on Mar. 5, 2004, now Pat. No. 8,070,750.

(51) Int. Cl.

| | |
|---|---|
| *A61B 17/00* | (2006.01) |
| *A61B 17/32* | (2006.01) |
| *A61B 17/16* | (2006.01) |
| *A61B 17/17* | (2006.01) |
| *A61B 17/34* | (2006.01) |
| *A61B 17/88* | (2006.01) |
| *A61B 19/00* | (2006.01) |

(52) U.S. Cl.
CPC ..... *A61B 17/320036* (2013.01); *A61B 17/1604* (2013.01); *A61B 17/1635* (2013.01); *A61B 17/1675* (2013.01); *A61B 17/1735* (2013.01); *A61B 17/1714* (2013.01); *A61B 17/1764* (2013.01); *A61B 17/320016* (2013.01); *A61B 17/3415* (2013.01); *A61B 17/8897* (2013.01); *A61B 2017/00424* (2013.01); *A61B 2019/462* (2013.01); *A61B 2019/547* (2013.01)

(58) Field of Classification Search
CPC .......... A61B 17/1604; A61B 17/1615; A61B 17/1659; A61B 17/1675
USPC ..................................................... 606/79–85
See application file for complete search history.

(56) References Cited

U.S. PATENT DOCUMENTS

| | | |
|---|---|---|
| 571,400 A | 11/1896 | Ruppert |
| 1,166,723 A | 1/1916 | Stark |
| 1,280,785 A | 10/1918 | McConnell |
| 1,289,722 A | 12/1918 | Fournier |
| 1,418,125 A | 5/1922 | Carroll |
| 1,471,062 A | 10/1923 | Riblett |
| 1,598,458 A | 8/1926 | Sullivan |

(Continued)

FOREIGN PATENT DOCUMENTS

| | | |
|---|---|---|
| EP | 0508710 | 5/1997 |
| JP | 9149907 | 6/1997 |

*Primary Examiner* — Mary Hoffman

(57) ABSTRACT

A tunnel notcher and guidewire delivery device is provided for creating a notch and positioning a guidewire within a bone tunnel. In general, the device includes an elongate member having proximal and distal ends with an inner lumen extending therebetween that is adapted to receive a guidewire. The device also includes a cutting element disposed on a distal portion of the elongate member that is adapted to remove bone within an opening of a bone tunnel. In use, the device 10 can be at least partially positioned within a bone tunnel containing a bone plug, and it can be manipulated to form a notch within or adjacent to an opening of the bone tunnel using the cutting element 18. The device 10 is also effective to deliver a guidewire 16 to the bone tunnel at a location adjacent to the notch.

13 Claims, 10 Drawing Sheets

(56) References Cited

U.S. PATENT DOCUMENTS

| | | |
|---|---|---|
| 1,781,863 A | 11/1930 | Shoemaker |
| 1,875,612 A | 9/1932 | Johnson |
| 2,009,795 A | 7/1935 | Graham |
| 2,250,434 A | 7/1941 | Dugaw |
| 2,465,305 A | 3/1949 | Cope |
| 3,043,002 A | 7/1962 | Brown |
| 3,088,454 A | 5/1963 | Shute |
| 3,554,192 A | 1/1971 | Isberner |
| 3,698,085 A | 10/1972 | Ray |
| 4,573,448 A | 3/1986 | Kambin |
| 4,586,496 A | 5/1986 | Keller |
| 4,603,694 A | 8/1986 | Wheeler |
| 4,881,537 A | 11/1989 | Henning |
| 4,978,349 A | 12/1990 | Frigg |
| 5,122,146 A | 6/1992 | Chapman |
| 5,374,269 A | 12/1994 | Rosenberg |
| 5,437,675 A | 8/1995 | Wilson |
| 5,632,747 A | 5/1997 | Scarborough |
| 5,643,273 A | 7/1997 | Clark |
| 5,645,545 A | 7/1997 | Bryant |
| 5,658,289 A | 8/1997 | Boucher |
| 5,807,276 A | 9/1998 | Russin |
| 5,868,684 A | 2/1999 | Akerfeldt |
| 5,908,422 A | 6/1999 | Bresina |
| 5,908,423 A | 6/1999 | Kashuba |
| 5,941,883 A | 8/1999 | Sklar |
| 6,036,695 A | 3/2000 | Smith |
| 6,110,175 A | 8/2000 | Scholl |
| 6,123,710 A | 9/2000 | Pinczewski |
| 6,270,501 B1 | 8/2001 | Freiberg |
| 6,409,730 B1 | 6/2002 | Green |
| 6,540,752 B1 | 4/2003 | Hicken |
| 6,770,079 B2 | 8/2004 | Bhatnagar |
| 7,041,107 B2 | 5/2006 | Pohjonen |
| 7,473,232 B2 | 1/2009 | Teague |
| 8,070,750 B2 | 12/2011 | Wenstrom |
| 2001/0016746 A1 | 8/2001 | McGuire |
| 2002/0019637 A1 | 2/2002 | Frey |
| 2002/0032447 A1 | 3/2002 | Weikel |
| 2002/0042624 A1 | 4/2002 | Johanson |
| 2002/0173795 A1 | 11/2002 | Sklar |
| 2004/0167527 A1 | 8/2004 | Simon |
| 2005/0159676 A1 | 7/2005 | Taylor |
| 2007/0106174 A1 | 5/2007 | Sanders |

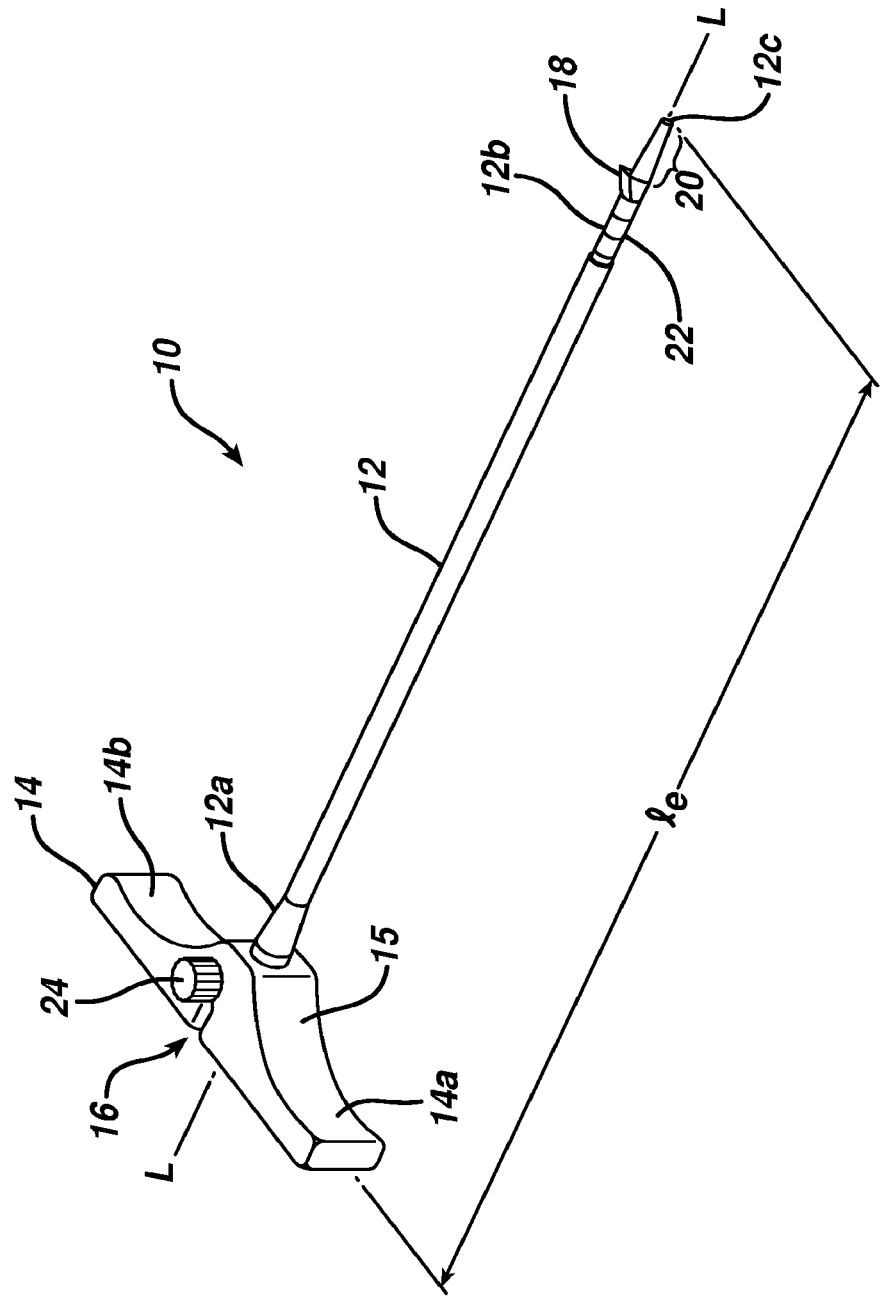

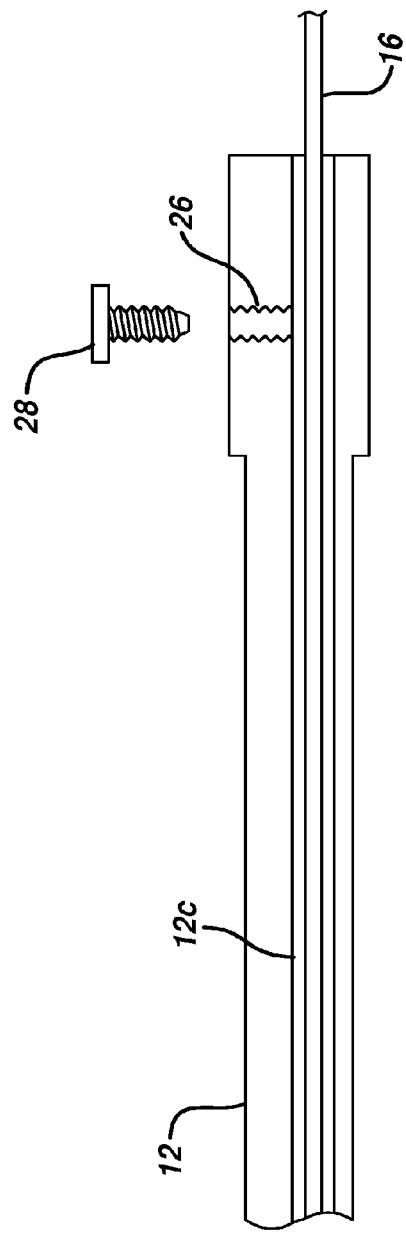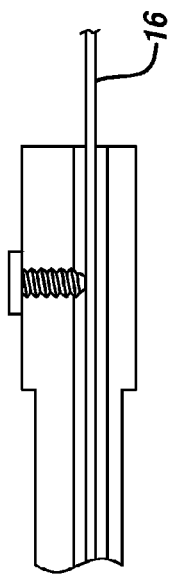
FIG. 3A
FIG. 3B

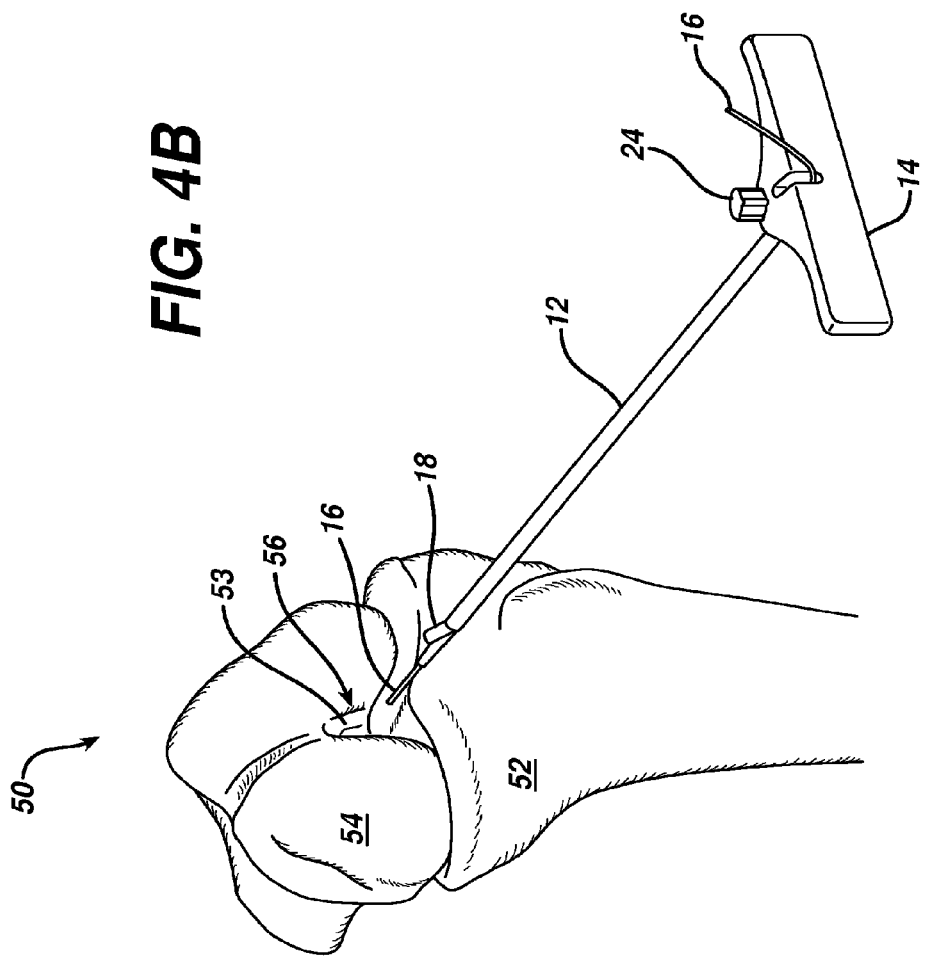

TUNNEL NOTCHER AND GUIDEWIRE DELIVERY DEVICE

CROSS REFERENCE TO RELATED APPLICATIONS

This application is a divisional application of U.S. patent application Ser. No. 10/708,467, entitled TUNNEL NOTCHER AND GUIDEWIRE DEVICE, filed Mar. 5, 2004, which is incorporated herein by reference.

FIELD OF THE INVENTION

The present invention relates to methods and devices for repairing torn and/or damaged tissue, and in particular to methods and devices for creating a notch and positioning a guidewire within a bone tunnel.

BACKGROUND OF THE INVENTION

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents or overexertion. Accordingly, various procedures have been developed to repair or replace such damaged ligaments. For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the ACL is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, and one end of the graft ligament is positioned in the femoral bone tunnel and the other end of the graft ligament is positioned in the tibial bone tunnel. The graft ligament thus extends between the femur and the tibia in substantially the same way, and with substantially the same function, as the original ACL, thereby allowing the graft ligament to cooperate with the surrounding anatomical structures so as to restore normal function to the knee.

When anchoring a graft ligament to the tibia and the femur, the two ends of the graft ligament are typically attached to an anchoring member, such as a bone plug, that is inserted into a bone tunnel. Bone screws or similar fasteners are often used to maintain each bone plug within its respective tunnel. Such a procedure typically requires a recess to be formed in the bone adjacent to the bone tunnel to allow the bone screw to be inserted alongside the bone plug. The recess serves as a "starter hole" for the bone screw so that the screw can engage bone in a generally proper direction with respect to the bone tunnel. As the bone screw is threaded into the bone, the resulting interference fit between the bone plug and the bone screw secures the graft ligament in place in the bone tunnel.

Since ACL repair is typically performed arthroscopically, the current procedure for forming a bone recess requires the surgeon to estimate the best location for positioning the bone screw adjacent to the bone plug. In particular, current devices for forming a recess in a bone tunnel have a relatively large size that requires that the recess be formed before the bone plug is inserted into the tunnel, thus the surgeon cannot determine the best location for the recess, and consequently for the bone screw, in relation to the bone plug. Once the recess is formed, a guidewire must be positioned between the anchoring member and a sidewall of the bone tunnel for delivering a bone screw to the tunnel at a location adjacent to the recess. Since the guidewire is delivered after formation of the notch, the position of the guidewire is often estimated as well. Accordingly, these methods and devices can result in misalignment of the bone screw, thus resulting in a high rate of divergence between the bone screw and the bone tunnel, and often in a loss of bone plug fixation within the bone tunnel. Unfortunately, screw/tunnel divergence is usually only identified postoperatively via radiographs, and the loss of bone plug fixation cannot be readily corrected, thereby resulting in an unsuccessful repair of a ruptured ACL.

Thus, there remains a need for improved methods and devices for creating a notch and positioning a guidewire within a bone tunnel to provide an accurate, secure, and trouble-free fixation of a ligament within the bone tunnel.

SUMMARY OF THE INVENTION

The present invention generally provides a tunnel notcher and guidewire delivery device for creating a notch and positioning a guidewire within a bone tunnel. In one embodiment, the device includes an elongate member having proximal and distal ends with an inner lumen extending therebetween and adapted to receive a guidewire. The device also includes a cutting element that is disposed on a distal portion of the elongate member and that is adapted to remove bone within an opening of a bone tunnel. A handle member can be disposed on or mated to a proximal portion of the elongate member. The device can also optionally include a locking mechanism that is adapted to lock a guidewire extending through the lumen in the elongate member in a releasably fixed position with respect to the elongate member. The locking mechanism can include, for example, a threaded member, such as a set screw, that is disposed within a threaded bore formed in the handle. The threaded bore is in communication with the inner lumen of the elongate member and it allows the set screw to secure the guidewire in the releasably fixed position.

The cutting element on the elongate member can be disposed at a variety of locations on the device, but in one embodiment, it is located on a distal portion of the distal end of the elongate member, and more preferably it is disposed proximal to the distal end of the elongate member. The cutting element can also have a variety of configurations, shapes, and sizes, but in an exemplary embodiment it is substantially wedge-shaped and extends distally outward from the elongate member. In an exemplary embodiment, the cutting element includes a distal-facing surface that is positioned at an acute angle with respect to a longitudinal axis of the elongate member. More preferably, the cutting element is adapted to create a notch in bone having a substantially semi-circular shape such that the notch is effective to facilitate placement of a bone screw within a bone tunnel for securing a bone plug therein.

The present invention also provides methods for preparing a bone tunnel. In one embodiment, the method includes the steps of positioning a tunnel notcher and guidewire delivery device between a bone plug and a sidewall of a bone tunnel and manipulating the device such that the cutting element removes a portion of bone to create a notch in or adjacent to an opening of the bone tunnel. The tunnel notcher and guidewire delivery device is then removed leaving a guidewire positioned between the bone plug and the bone tunnel adjacent to the notch. A bone screw can then be delivered along the guidewire to engage bone at the notch, and thereby secure the bone plug within the bone tunnel.

BRIEF DESCRIPTION OF THE DRAWINGS

The invention will be more fully understood from the following detailed description taken in conjunction with the accompanying drawings, in which:

FIG. 1 is a perspective view of one embodiment of a tunnel notcher and guidewire delivery device according to the present invention;

FIG. 3A is cross-sectional view of a locking mechanism on the tunnel notcher and guidewire delivery device shown in FIG. 1;

FIG. 3B is a cross-sectional view of the locking mechanism shown in FIG. 3A in the locked position;

FIG. 4B is an illustration of the human knee shown in FIG. 4A with a tunnel notcher and guidewire delivery device in accordance with the present invention being introduced into the bone tunnel;

DETAILED DESCRIPTION OF THE INVENTION

Figure 2A:
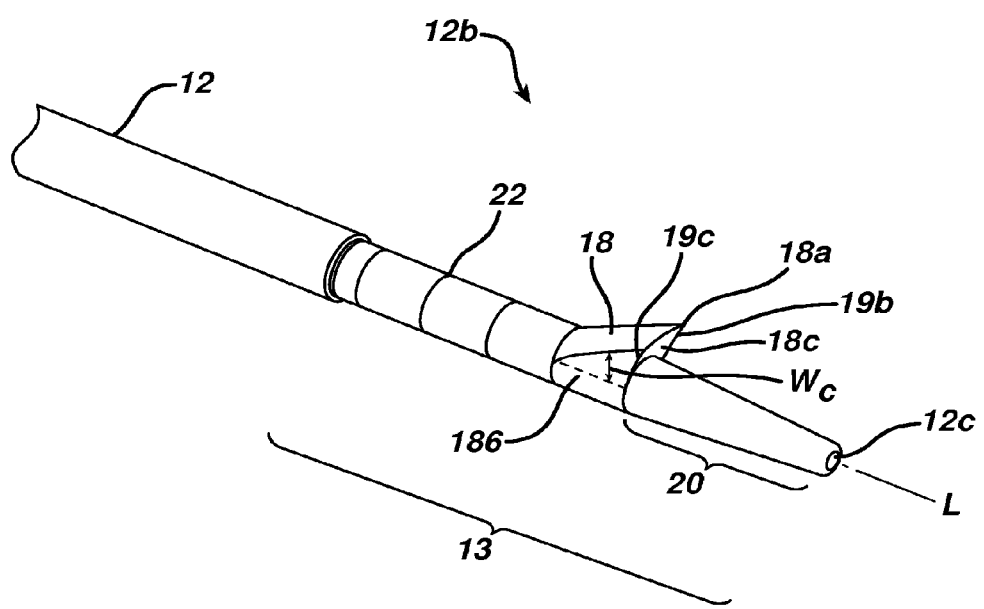
FIG. 2A is an enlarged view of a cutting element on the tunnel notcher and guidewire delivery device shown in FIG. 1.

The present invention provides a device for creating a notch in a bone tunnel, and for positioning a guidewire within the bone tunnel. In general, as shown in FIG. 1, the device 10 includes an elongate member 12 having an inner lumen 12c extending therethrough and adapted to receive a guidewire 16. A cutting element 18 is formed on or adjacent to a distal portion 13 of the elongate member 12, and it is effective to remove bone within or adjacent to an opening of a bone tunnel. The device 10 can also include a handle 14 mated to or formed on a proximal end 12a of the elongate member 12 for grasping the device 10. In use, the device 10 can be at least partially positioned within a bone tunnel containing a bone plug, and it can be manipulated to form a notch within or adjacent to an opening of the bone tunnel using the cutting element 18. The device 10 is also effective to deliver a guidewire 16 to the bone tunnel at a location adjacent to the notch. The guidewire 16 can subsequently be used to deliver a fastening element, such as a bone screw, to the notch, thus allowing the bone screw to be threaded into the bone tunnel to secure the bone plug or other anchoring member within the tunnel.

The methods and devices of the present invention are particularly advantageous in that they allow a surgeon to remove bone to form a notch within or adjacent to an opening of a bone tunnel after a bone plug or other anchoring member has been positioned in the bone tunnel, thereby ensuring proper positioning of the notch and subsequently of a fastening element with respect to the bone plug. The device 10 also eliminates the additional step of positioning a guidewire after the notch is formed since the guidewire is implanted using the tunnel notcher and guidewire delivery device, thus further providing proper alignment of the bone screw with the notch and the bone plug or other anchoring member disposed within the bone tunnel.

Still referring to FIG. 1, the elongate member 12 of the tunnel notcher and guidewire delivery device 10 can have a variety of configurations, shapes, and sizes. As shown in FIG. 1, however, the elongate member 12 has a generally hollow cylindrical shape and it includes proximal and distal ends 12a, 12b with an inner lumen 12c extending therebetween for slidably receiving a guidewire 16. The length $l_e$ of the elongate member 12 can vary, but it should be sufficient to allow the proximal end 12a of the elongate member 12 to remain outside a patient's body while the distal end 12b is positioned within a bone tunnel, preferably between a bone plug or other anchoring member and a sidewall of the bone tunnel.

The proximal end 12a of the elongate member 12 preferably has a handle 14 mated thereto or formed thereon to facilitate grasping the device 10. While the handle 14 can have any shape and size, FIG. 1 illustrates a generally elongate handle 14 that extends in a direction that is substantially transverse to a longitudinal axis L of the elongate member 12. Opposed gripping portions 14a, 14b, can be formed on the handle 14 to conform to a user's fingers. In particular, a distal-facing surface 15 of each gripping portion 14a, 14b, can be substantially concave for seating one or more fingers of the user. This allows the user to grasp the device 10 by positioning their fingers around the handle 14 so as to form a fist. A person skilled in the art will appreciate that a variety of handles or other devices can be used to facilitate grasping of the device 10.

Figure 2B:
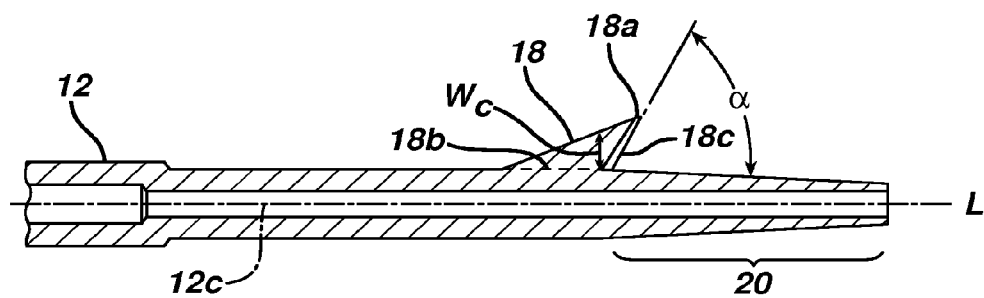
FIG. 2B is a side, cross-sectional view of the cutting element shown in FIG. 2A taken along a longitudinal axis of the tunnel notcher and guidewire delivery device.

The distal end 12b of the elongate member 12 can also have a variety of configurations, but it should be adapted to be positioned between a bone tunnel and a bone plug or other anchoring member. The distal end 12b is also preferably configured such that at least a portion of it can be inserted into the bone tunnel to a particular depth to facilitate the correct positioning of the cutting element 18 with respect to the bone tunnel. In an exemplary embodiment, shown in FIGS. 2A and 2B, the distal end 12b has a tapered tip 20 such that a diameter of the tip 20 decreases in a proximal to distal direction. This facilitates insertion of the distal end 12b between the sidewall of the bone tunnel and the anchoring member. The distal end 12b can also include markings 22 or other indicia disposed or formed thereon, as shown in FIGS. 1 and 2A, to indicate an insertion depth of the distal end 12b of the elongate member 12 into a bone tunnel. The markings 22, which are preferably located proximal to the cutting element 18, can optionally extend circumferentially around the elongate member 12 to facilitate visual access thereof. In an exemplary embodiment, the markings 22 are radio-opaque to allow x-ray visualization thereof during an arthroscopic procedure.

Figure 2C:
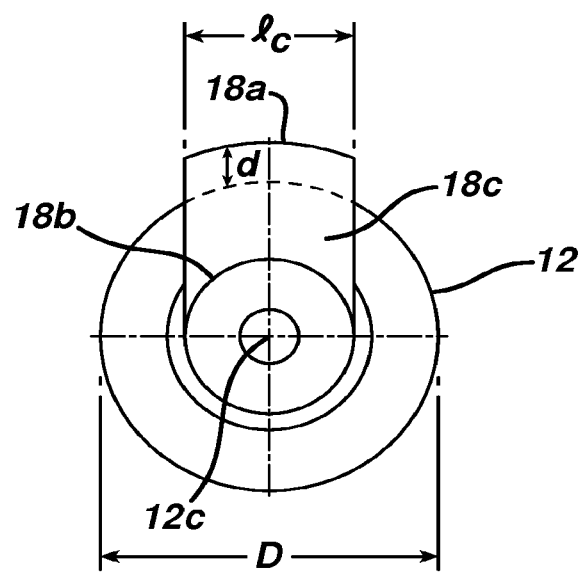
FIG. 2C is an end view of the tunnel notcher and guidewire delivery device shown in FIG. 1.

As previously stated, the device 10 also includes a cutting element 18 that is formed on a distal portion 13 of the elongate member 12. The cutting element 18, which is shown in more detail in FIGS. 2A-2C, can have any configuration and it can be disposed anywhere on the elongate member, but it should be effective to remove bone to form a notch adjacent to or within an opening of a bone tunnel. In an exemplary embodiment, as shown, the cutting element 18 is positioned proximal to the distal end 12b of the elongate member 12, preferably just proximal to the tapered tip 20, to allow the tapered tip 20 to be disposed into a bone tunnel between a sidewall of the bone tunnel and a bone plug or other anchoring member disposed therein. The cutting element is also preferably disposed on one side of the elongate member 12, such that it is offset from the longitudinal axis L of the elongate member 12. In particular, the cutting element 18 can have a length $l_c$ (FIG. 2C) that is less than or equal to a diameter D of the elongate member 12. Such a configuration will allow the cutting element 18 to remove bone from the bone tunnel without coming into contact with and/or causing damage to the bone plug or other anchoring member disposed within the bone tunnel.

The shape and size of the cutting element 18 can also vary, but in an exemplary embodiment it is substantially wedge-shaped such that it has a width $w_c$ that increases in a proximal to distal direction. A base portion 18b of the cutting element 18 is mated to or formed on the elongate member 12, and a cutting edge 18a is positioned a distance d apart from the elongate member 12. The distance d (FIG. 2C) between the cutting edge 18a and the elongate member 12 can vary, but it should be sufficient to allow a portion of bone adjacent to or within a bone tunnel to be removed such that a notch is created for receiving a bone screw. The cutting edge 18a is also preferably positioned at a location that is distal of the base portion 18b with respect to the longitudinal axis L of the elongate member 12. This can be achieved by providing a distal-facing surface 18c on the cutting element 18 that extends between the cutting edge 18a and the elongate member 12, and that is positioned at an acute angle α with respect to the longitudinal axis L of the elongate member 12. While the angle α can vary, in an exemplary embodiment, the angle α is in the range of about 20° to 70°. The distal-facing surface 18c can also optionally be substantially concave such that opposed edges 19a, 19b of the cutting element 18 form cutting edges that are effective to remove bone.

In another embodiment, the cutting edge 18a can have a substantially arcuate shape, such that the distance d between the cutting edge 18a and the elongate member 12 remains substantially constant along the entire length $l_c$ of the cutting edge 18a. Such curvature of the cutting edge 18a will facilitate removal of bone, and in particular it will allow a semi-circular notch to be formed in bone.

As previously stated, the tunnel notcher and guidewire delivery device 10 includes an inner lumen 12c that extends through the elongate member 12 and the handle 14 for receiving a guidewire. Since the guidewire is preferably positioned within the inner lumen 12c during use of the device 10, the device 10 can optionally include a locking mechanism 24 formed thereon for maintaining a guidewire in a fixed position relative to the elongate member 12. While a variety of locking mechanisms known in the art can be used, FIGS. 1 and 3A-3B illustrate an exemplary embodiment of a locking mechanism 24 that is formed on the handle 14 of the elongate member 12. As shown, the locking mechanism 24 is in the form of a set screw 28 that is disposed within a threaded bore 26 formed in handle 14. The threaded bore 26 is in communication with the inner lumen 12c of the elongate member 12. In use, as shown in FIG. 3B, the set screw 28 can be threaded into the threaded bore 26 to engage a guidewire 16 that is disposed within the inner lumen 12c of the elongate member 12, thereby locking the guidewire 16 in a fixed position.

The tunnel notcher and guidewire delivery device 10 of the present invention can be used in a variety of medical procedures for preparing a bone tunnel for receiving a fastening element, such as a bone screw, to secure an anchoring member disposed within the bone tunnel. In an exemplary embodiment, however, the device 10 is used to prepare a bone tunnel for anchoring a ligament therein, and in particular for arthroscopic femoral fixation of an anterior cruciate ligament (ACL) graft, as shown in FIGS. 4A-4E. While various graft ligaments can be used, the graft ligament (not shown) is typically prepared by separating the graft into four tendon bundles, each of which is prepared by whip stitching a length of suture thereto. Two anchoring members, such as bone plugs, are then attached at each end of the ligament.

An incision is then made, following medically acceptable patient preparation and anesthetization, near the end of the tibial bone 52 below the patella, and a bone tunnel 56 is formed through the tibial and femoral bones 52, 54. For illustration purposes, FIGS. 4A-4E only show a bone tunnel 56 formed in the femoral bone 54, however, a person skilled in the art will appreciate that the device and methods of the present invention can be inserted through either or both of the femoral and tibial bones. One end of the graft ligament, i.e., the leading end, is then passed through the tibial tunnel into the femoral tunnel 56, and the other end of the graft ligament, i.e., the trailing end, remains outside of the tibial bone tunnel, thus permitting access through the tibial tunnel to the femoral tunnel 56. Again, for illustration purposes, FIGS. 4A-4E only show a bone plug 53 disposed within the femoral bone tunnel 56, and a graft ligament is not shown.

In preparation for use, a guidewire 16 is inserted through the device 10 of the present invention, preferably such that a portion of the guidewire 16 extends from the distal end 12b of the elongate member 12 to facilitate insertion of the distal tip 20 of the device 10 into the bone tunnel 56 between the bone plug 53 and a sidewall of the bone tunnel 56. The guidewire 16 is preferably locked in fixed position by rotating the set screw 28 of the locking mechanism 24. Since most guidewires are relatively flexible, it is preferable to only have a small portion of the guidewire 16 extend from the distal end 12b of the elongate member 12 to provide rigidity to the guidewire 16.

Figure 4A:
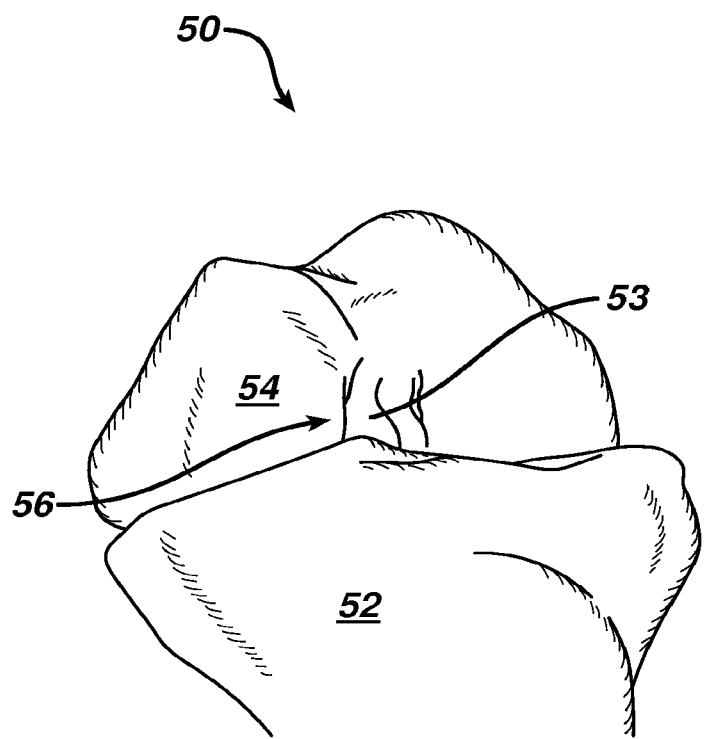
FIG. 4A is an illustration of a human knee having a bone tunnel formed therein.
Figure 4C:
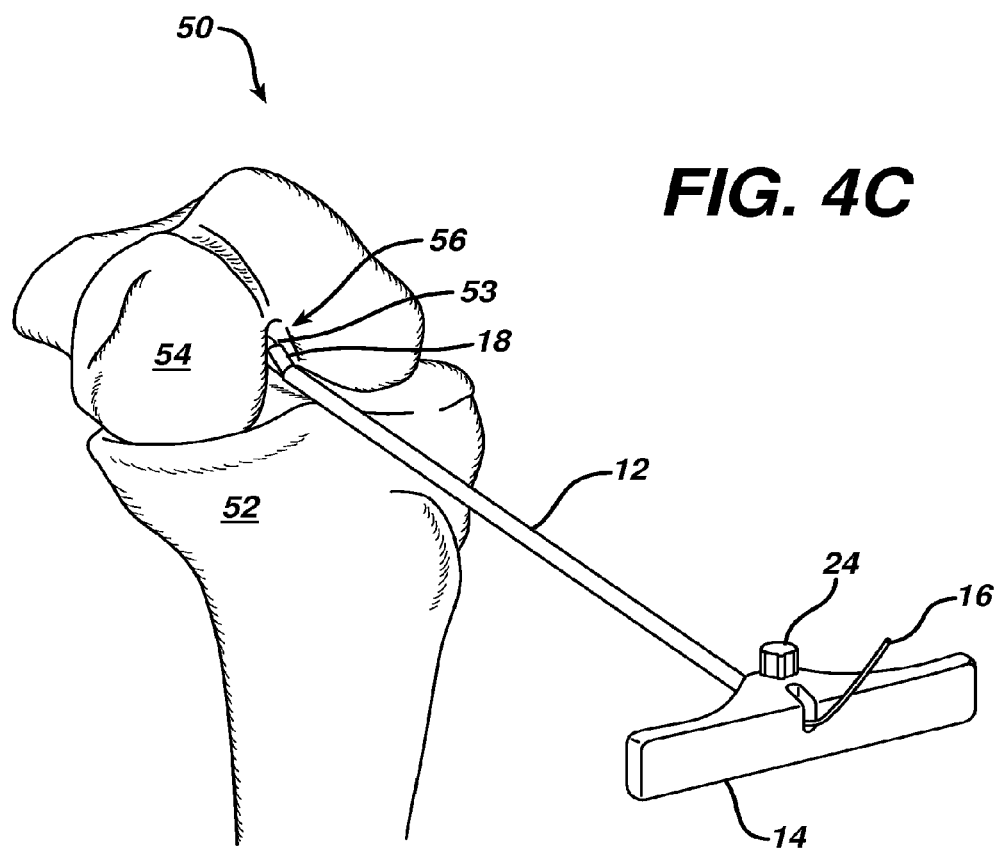
FIG. 4C is an illustration showing the tunnel notcher and guidewire delivery device of FIG. 4B disposed within the bone tunnel to remove bone, forming a notch within the opening of the bone tunnel.

The device 10 can then be inserted through the tibial bone tunnel 56 to position the tapered tip 20 of the elongate member 12 between the bone plug 53 and the femoral bone tunnel 56, as illustrated in FIGS. 4B and 4C. A mallet or other impacting tool can optionally be used to further impact the device 10 to advance it into the area between the bone plug 53 and the bone tunnel 56 to a desired depth. The radio-opaque markings 22 near the distal end 12b of the elongate member 12 can be used to indicate when the device 10 is at the correct depth.

Figure 4D:
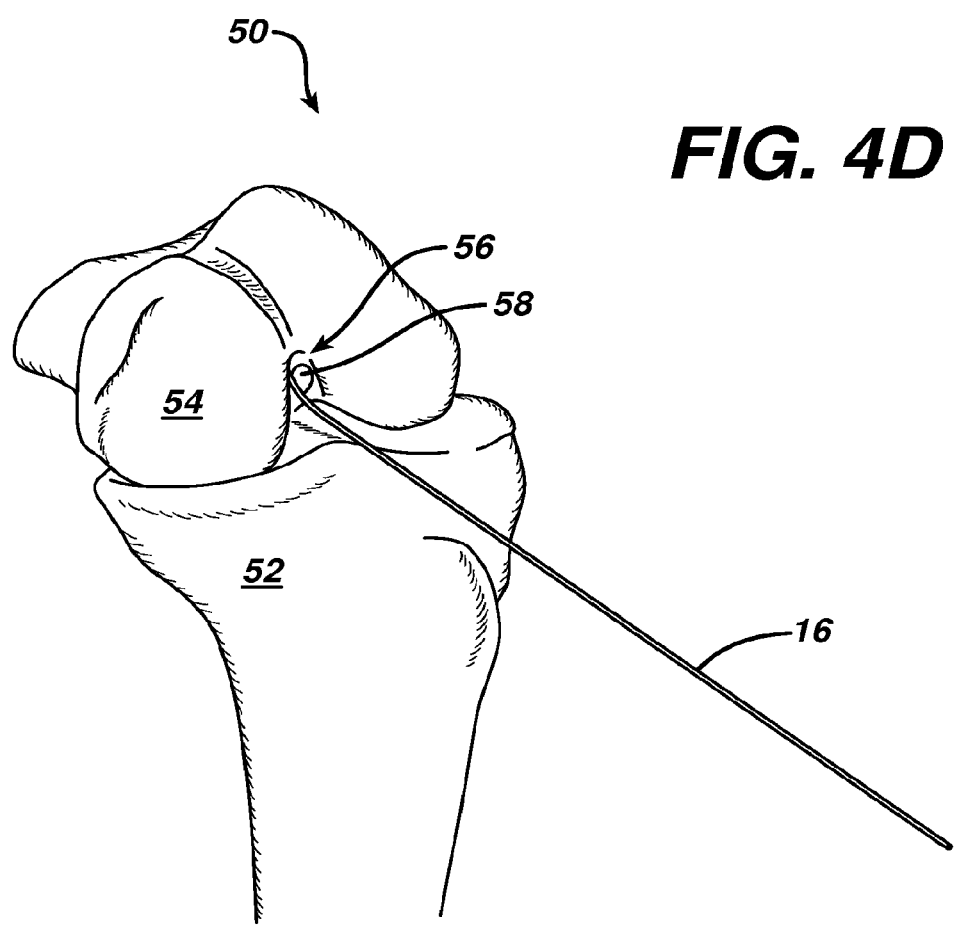
FIG. 4D is an illustration showing the tunnel notcher and guidewire delivery device of FIG. 4C removed from the bone tunnel, leaving a guide wire positioned within the bone tunnel adjacent to the notch.

Once properly positioned, the device 10 is partially rotated about its longitudinal axis L such that cutting edge 18a of the cutting element 18 moves in a semi-circular direction, thereby removing a portion of bone to create a notch 58. As shown in FIG. 4D, the notch 58 is formed within or adjacent to an opening of the bone tunnel 56. After creating the notch 58, the locking mechanism 24 is released by rotating the set screw 28 in the opposite direction, allowing the device 10 to be removed while leaving the guidewire 16 positioned within the bone tunnel 56, as illustrated by FIG. 4D, between the bone plug 53 and adjacent to the notch 58.

Figure 4E:
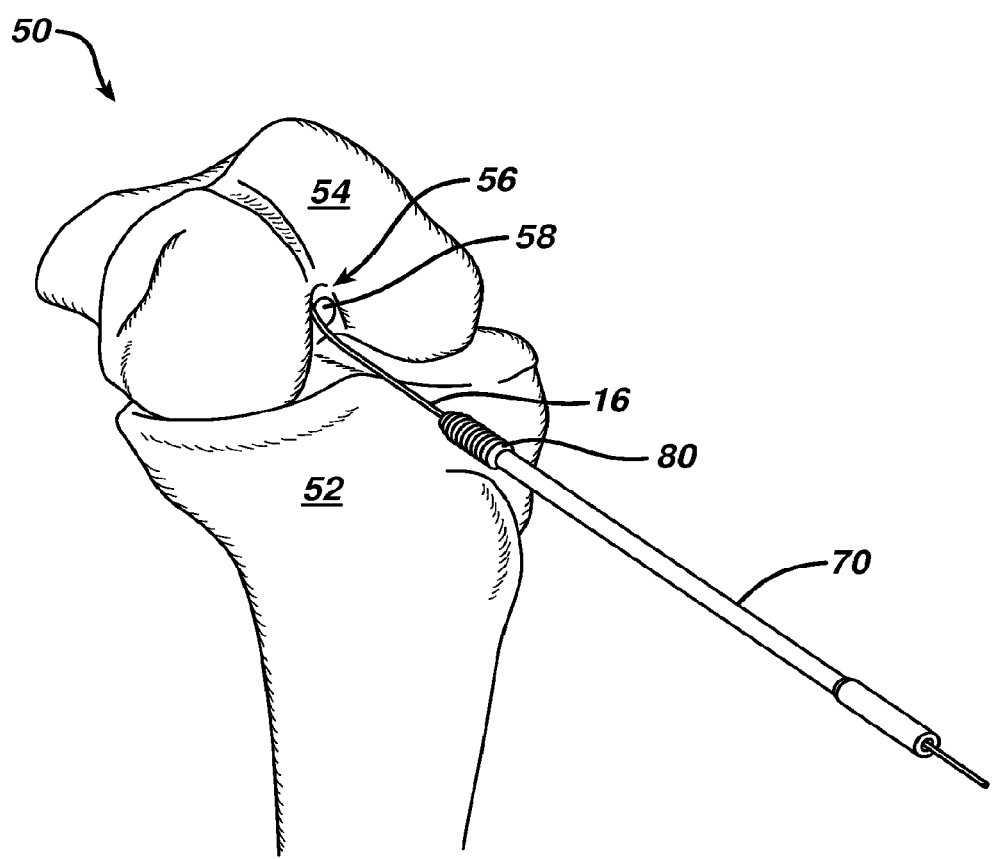
FIG. 4E is an illustration showing a bone screw being delivered along the guide wire shown in FIG. 4D to the bone tunnel in accordance with another embodiment of the present invention.

A fastening element, such as a bone screw 80, as shown in FIG. 4E, can then be delivered by sliding the screw 80 along the guidewire 16 toward the notch 58. An insertion tool or driver mechanism 70, as shown, can optionally be used to advance the screw 80 along the guidewire 16, and to thread the screw 80 into the bone tunnel 56. When the bone screw 80 is positioned adjacent to the bone tunnel 56, the notch 58 will allow the threads of the bone screw 80 to engage the bone, and thus further rotation of the screw 80 will engage the bone plug 53 in the bone tunnel 56.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for preparing a bone tunnel, comprising:
   inserting a bone plug into a bone tunnel;
   positioning a tunnel notcher and guidewire delivery device between the bone plug and a sidewall of the bone tunnel, the tunnel notcher comprising an elongate member with an inner lumen extending therethrough, a guidewire passing through the lumen, and further comprising a cutting element having a distal bone cutting edge disposed proximal to a distal portion of the elongate member, the cutting edge facing distally and being entirely spaced away from and not normal to the elongate member;
   removing a portion of bone with the cutting edge to create a notch in an opening of a bone tunnel, the notch being effective to facilitate placement of a bone screw within the bone tunnel for securing the bone plug therein; and
   removing the tunnel notcher and guidewire delivery device such that the guidewire remains positioned between the bone plug and the bone tunnel adjacent to the notch.

2. The method of claim 1, wherein the notch has a substantially semi-circular shape.

3. The method of claim 1, further comprising delivering a bone screw along the guidewire to engage bone at the notch, and to secure the bone plug within the bone tunnel.

4. The method of claim 1, wherein the guidewire is disposed within the tunnel notcher and guidewire delivery device during positioning of the tunnel notcher and guidewire delivery device between the bone plug and the bone tunnel.

5. The method of claim 4, wherein the guidewire is in a releasably fixed position with respect to the tunnel notcher and guidewire delivery device during positioning of the tunnel notcher and guidewire delivery device between the bone plug and the bone tunnel.

6. The method of claim 5, further comprising a locking mechanism formed on the tunnel notcher and guidewire delivery device and adapted to releasably fix the guidewire with respect to the tunnel notcher and guidewire delivery device.

7. The method of claim 6, wherein the locking mechanism is coupled to a handle formed on the tunnel notcher and guidewire delivery device.

8. The method of claim 7, wherein the locking mechanism comprises a threaded member disposed within a threaded bore formed in the handle, the threaded bore being in communication with an inner lumen formed in the tunnel notcher and guidewire delivery device and containing the guidewire.

9. The method of claim 1, wherein a distal portion of the tunnel notcher and guidewire delivery device is substantially tapered to allow the distal portion to be positioned between the bone plug and the sidewall of the bone tunnel.

10. The method of claim 1, wherein the cutting element extends distally outward from the tunnel notcher.

11. The method of claim 10, wherein the cutting element is substantially wedge-shaped and includes a distal-facing surface that is disposed at an acute angle with respect to a longitudinal axis of the tunnel notcher.

12. The method of claim 11, wherein the angle is less than 90°.

13. The method of claim 1, further comprising a plurality of indicia formed on a distal portion of the tunnel notcher and guidewire delivery device and adapted to indicate a depth of the tunnel notcher and guidewire delivery device within a bone tunnel.

* * * * *